US009675554B1

(12) United States Patent
Gregoriadis et al.

(10) Patent No.: US 9,675,554 B1
(45) Date of Patent: Jun. 13, 2017

(54) METHOD OF FORMING LIPOSOMES

(75) Inventors: Gregory Gregoriadis, London (GB); Brahim Zadi, London (GB); Pramukh N Jayasekera, Salisbury (GB)

(73) Assignee: The Secretary of State for Defence in Her Britannic Majesty's Government of the United Kingdom of Great Britain and Northern Ireland, Farnborough, Hampshire (GB)

( * ) Notice: Subject to any disclaimer, the term of this patent is extended or adjusted under 35 U.S.C. 154(b) by 1826 days.

(21) Appl. No.: 09/719,795

(22) PCT Filed: Jun. 16, 1999

(86) PCT No.: PCT/GB99/01911
§ 371 (c)(1),
(2), (4) Date: Dec. 18, 2000

(87) PCT Pub. No.: WO99/65465
PCT Pub. Date: Dec. 23, 1999

(30) Foreign Application Priority Data

Jun. 18, 1998 (GB) .................................... 9813100.6

(51) Int. Cl.
*A61K 9/127* (2006.01)

(52) U.S. Cl.
CPC ............ *A61K 9/127* (2013.01); *A61K 9/1271* (2013.01)

(58) Field of Classification Search
USPC ......... 424/450, 417, 1.21, 9.321, 9.51, 94.3; 436/829; 935/54; 264/4.1, 4.3, 4.6
See application file for complete search history.

(56) References Cited

U.S. PATENT DOCUMENTS

| 4,857,319 | A | * | 8/1989 | Crowe et al. ................ 424/94.1 |
| 5,089,181 | A | * | 2/1992 | Hauser | |
| 5,612,057 | A | * | 3/1997 | Lanza | |
| 5,817,334 | A | * | 10/1998 | Schmidt | |
| 5,958,881 | A | * | 9/1999 | Korman ......................... 514/12 |
| 6,083,530 | A | * | 7/2000 | Mayer et al. ................. 424/450 |
| 6,475,517 | B1 | * | 11/2002 | Tagawa et al. ............... 424/450 |

FOREIGN PATENT DOCUMENTS

| EP | 0 800 822 A | 10/1997 |
| WO | 86/01103 | 2/1986 |
| WO | 97/35561 A | 10/1997 |

OTHER PUBLICATIONS

Zadi, Brahim et al.: "A novel method for high-yield entrapment of solutes into small liposomes" Proc. Int. Symp. Controlled Release Bioact. Mater. (1998), 25$^{th}$, 402-403.

* cited by examiner

*Primary Examiner* — Gollamudi Kishore
(74) *Attorney, Agent, or Firm* — Morrison & Foerster LLP

(57) ABSTRACT

Compositions of reagents are formed by forming empty liposomes, mixing the thus-formed liposomes with a sugar solution and a regent, then drying the mixture. The compositions will generally contain less than 10% w/v sucrose. Using this procedure small liposomes are formed with high entrapment efficiency. The process is useful in the production of pharmaceuticals.

7 Claims, 3 Drawing Sheets

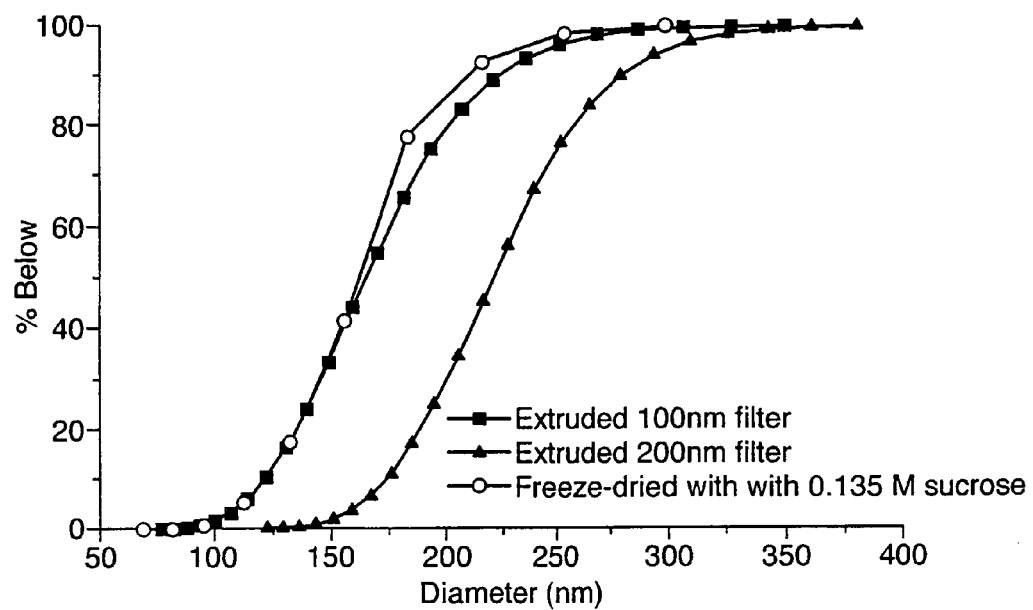
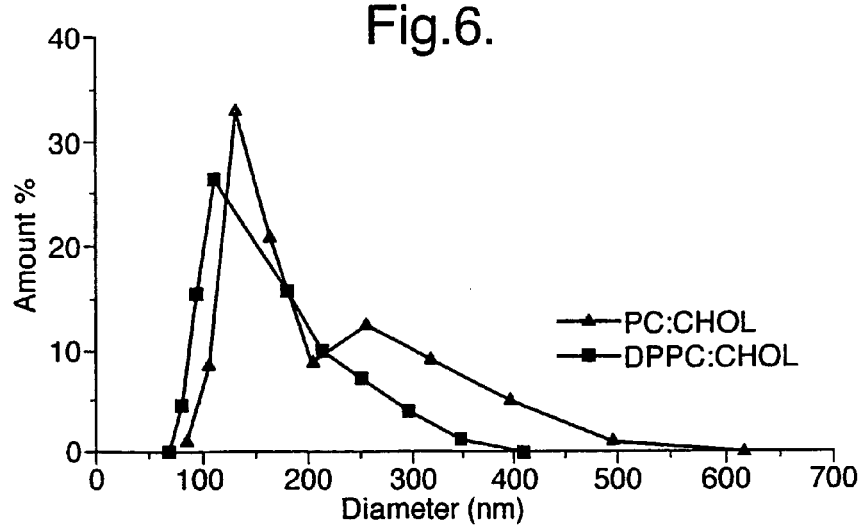

METHOD OF FORMING LIPOSOMES

The present invention relates to a method of forming liposomes, to liposomes obtained thereby and their use, in particular in pharmaceutical applications.

The use of liposomes is well known in a wide variety of fields, including the pharmaceutical and cosmetic fields, where they are used as carriers for drugs and other reagents which are suitable for application to the skin.

Various methods are known for preparing liposomes. For example, they may be prepared by a dehydration/rehydration technique in which a lipid is dissolved in an organic solvent such as chloroform, dichloromethane or an alcohol such as methanol or ethanol. The solution is then dried for example using a rotary evaporator, in order to form a film of lipid on the wall of the evaporator vessel. Addition of water or an aqueous solution such as a buffer to the dry film results in the formation of multilamellar liposomes. This forms a first step in the production of vesicles using various methods. Subsequent treatment may lead to dehydration/rehydration vesicles or DRVs (Kirby and Gregoriadis, Biotechnology (1984) 2, 979-984). Alternatively, subsequent treatment by sonication of lipid suspensions to form for example unilamellar liposomes (A. D. Bangham et al., J. Mol. Biol. 13, 238 (1965)).

Other methods, which are well documented in the art, include detergent removal (Y. Kagawa et al., J. Biol. Chem. (1971 246, 5477), reverse-phase evaporation (F. Szoka and D. Papahadjopoulos, Proc. Natl. Acad. Sci, USA (1978) 75, 4194) and ether injection (D. Deamer et al., Biochim. Biophys. Acta, (1976) 433, 629) as well as the freeze drying methods (see for example Ohsawa et al., Chem. Pharm. Bull, (1984) 32, 2442-5 and Kirby and Gregoriadis (1984) supra.) and freeze thawing methods (D. D. Lasic "Liposomes: from Physics to Application, Elsevier, 1993, p98).

Different methods of preparation lead to liposomes of different sizes and other characteristics. Liposomes can be used to encapsulate materials such as biologically active materials such as pharmaceuticals including vaccines, as well as non-pharmaceutical agents such as materials which affect skin, such as artificial tanning preparations and other beauty aids. Encapsulation techniques vary depending upon the nature of the reagent to be encapsulated and the size and characteristics of the generated liposome.

The size of liposomes is important in terms of their application. In some instances, large liposomes may be required, for example, where particulates including microorganisms such as bacteria are to be encapsulated for example for vaccine use as described in WO 95/09619.

Small liposomes however are preferable for many applications. This is because small liposomes are removed by the reticulo-endothelial system (RES) less rapidly and to a lower extent compared to large liposomes (over 200 nm in size). The uptake by the RES increases with the size of the vesicles. Furthermore large liposomes injected intramuscularly are unable to reach the regional lymph nodes with good efficiency and to deliver vaccines and other agents to these sites (Gregoriadis G. Liposomes as Drug Carriers: Recent Trends and Progress, Wiley Chichester 1988).

Liposome formulations of various drugs can be optimized in terms of drug content, stability, biodistribution patterns and cellular uptake by changing physicochemical parameters of liposomes such as phase transition temperature, size, size distribution, surface charge, surface hydration with compounds bearing hydrophilic groups and size distribution.

Liposome size is a parameter which determines the fraction cleared by the RES (Senior et al. Biochem., Biophys, Acta (1985) 839, 1-8; Nagayasu et al., Biol. Pharm. Bull. (1995) 18(7), 1020-1023. Small liposomes can be prepared by the use of high pressure homogenizers (Talsma et al. Drug Development and Industrial Pharmacy (1989) 15(2) 197-207, Vemuri S et al. Drug Development and Industrial Pharmacy (1990) 16(15), 2243-2256) but large amount of lipids have been used in order to achieve an acceptable entrapped drug to lipid mass ratio. In another approach (Gregoriadis et al., Int. J. Pharm. 65 (1990) 235-242), the microfluidization of multilamellar dehydration-rehydration vesicles (DRVs) in the presence of unencapsulated drug produced vesicles with sizes less than 200 nm., retaining quantities of the originally entrapped solute.

The vesicle stabilization effect of adding sugar after preparation of liposomes has been established (Crowe L. M. et al. Arch. Biochem. Biophys. 242 (1985) 240-247, Hauser et al. Biochem. Biophys. Acta (1987) 897, 331-334), for instance when drug containing liposomes are freeze dried for storage and then rehydrated for use.

The applicants have found an improved way of preparing liposomes and particularly small liposomes, which reduces the number of preparation steps and forms stable liposomes, with high entrapment efficiency.

According to the present invention there is provided a method of producing a liposome preparation of a reagent, which method comprises the steps of
(i) forming empty liposomes;
(ii) mixing the liposomes from step (i) with a sugar solution and said reagent; and
(iii) drying the mixture from step (ii).

On rehydration of the dried material from step (iii), liposomes, encapsulating the reagent are formed. The increase in size of the liposomes thus obtained as compared to the liposomes obtained in step (i) is much lower when compared to the liposomes in preparations which do not include a sugar. The need for further extrusion, microfluidisation or homogenisation steps as outlined above may thus be avoided.

It is established that during drying in the presence of appropriate concentrations of sugars, fusion and aggregation of liposomes is prevented to a certain extent by the formation of an amorphous glass (Crowe et al Arch. Biochem. Biophys. 242 (1985) 240-247) and interaction of sugar with the phospholipid headgroups (Crowe et al. Cryobiology 31 (1994) 355-366). In early studies dehydration/rehydration vesicles (DRV's) were performed without using sugars as stabilizers, the procedure being based on induction of fusion/aggregation of performed small unilamellar vesicles upon controlled rehydration (Kirby Gregoriadis, 1984). On this basis, one could predict that the total stabilization of small unilamellar vesicles by the presence of appropriate amounts of sugars will lead upon reconstitution to the original SUV's to a very low entrapment.

This has unexpectedly not found to be the case. Although as with all liposomes, the degree of entrapment of reagent depends to some extent on the ratio lipid:reagent in the system, the amount of reagent which is encapsulated within the liposomes obtained using the method of the invention is expected to be good.

Furthermore, physical and chemical stability of liposomes is required for their application as a drug delivery system. Liposomes in the state of aqueous dispersions are subjected to hydrolysis and physical changes during storage including leakage of encapsulated drugs, and changes in vesicle size due to aggregation or fusion. The physical and chemical stability of liposomes produced by the method of the invention is expected to be good.

Thus this method gives rise to the possibility of obtaining small highly loaded vesicles or liposomes, which, as outlined above, may be particularly useful in the formation of pharmaceutical compositions. Thus this method may be used to prepare encapsulated materials of many types.

It is particularly suitable however for the production of small liposomes for pharmaceutical use. In this case, the reagents used in the method will comprise a biologically active material such as a pharmaceutical or drug. For this purpose, the liposomes obtained in step (i) are suitably small unilamellar vesicles with an average size, for example in the range of from 25 nm to 90 nm, preferably in the range of from 50 to 90 nm and conveniently from 70 to 90 nm. Liposomes obtained ultimately from the process of the invention will still be small, with average size of less than 500 nm, usually from 100-200 nm.

The liposomes used in step (i) are empty liposomes, obtained by any of the conventional methods, for example using a classical method as described above. Any liposomes which are produced which have an average size which is too large for the desired purpose, may be reduced for example using sonication, homogenisation, extrusion or microfluidisation techniques as are known in the art.

Lipids used in the production of the liposomes are well known in the art. They include for example, lecithins such as phosphatidylcholine (PC), dipalmitoyl phosphatidylcholine (DPPC), distearoyl phosphatidylcholine (DSPC) or charged lipids in particular anionic lipids such as phosphatidic acid or cationic lipids such as stearylamine, optionally in the presence of cholesterol. A further preferred lipid is DSPC. The selection of lipid will depend, to some extent on the nature of the active agent and the intended purpose of the liposome.

Suitable sugar solutions for use in step (ii) include aqueous solutions of monosaccharides such as glucose and fructose, disaccharides such as lactose or sucrose as well as polysaccharides. A particularly preferred sugar for use in the method of the invention is a disaccharide such as sucrose or lactose or a monosaccharide such as glucose. In particular, the sugar is sucrose.

Suitably the amount of sugar used in step (ii) is such that the mass ratio of sugar to lipid is in the range of from 1:1 to 6:1 w/w, suitably from 1:1 to 5:1 w/w. It has been found that the greater the amount of sugar present, the lower the increase in size of the liposomes obtained following rehydration as compared to those obtained in step (i). However, the degree of entrapment of the reagent may be lower. Thus the precise selection of ratios used will depend upon the required end use, with a balance being determined between the degree of entrapment for a given lipid content and liposome size. The difference this makes to the liposome formation varies to a certain extent, depending upon the particular reagent employed as discussed further below. Suitably, the amount of sugar present is less than 10% w/v of the composition.

It has further been found that increasing the volume of the sugar solution used in the process, by reducing the concentration of the sugar solution, may enhance entrapment. Suitable concentrations of sugar solutions are from 20 to 200 mM, preferably from 30 to 150 mM.

In addition, it has been found that if the subsequent rehydration is effected at elevated temperatures, for example of from 30 to 80° C., in particular from 40 to 65° C. and especially at about 60° C., entrapment values can be increased. This has been found to be effective with liposomes comprising PC and CHOL, which would usually be formed at room temperature. There may be some size increase as compared to the starting liposomes when using elevated temperatures in this way, and therefore, this should be taken into account in selecting the particular conditions used to produce liposomes in any particular case.

Other factors which have been found to affect entrapment include the particular nature of the reagent, such as the drug, being encapsulated and in particular, its solubility, and the amount of reagent present. The solubility of the reagent, may in some instances, limit the amount that can be dissolved in step (ii) and thus entrapped in the liposome. Other factors which affect the amount of reagents which are entrapped include the interactions of the reagent with the lipids forming the liposome, and the permeability of the liposome to the reagent.

Where high concentrations of reagent are present in the solution used in step (ii) of the reaction, the percentage entrapment may be lower. Therefore, for reasons of economy, there may be an advantage in reducing the amount of reagent used.

The selection of conditions which will give liposomes of the desired size and loading, including the sugar: lipid mass ratio, the selection of lipid, the concentration of the sugar solution used, the amount of reagent included in the solution, and the temperature of rehydration, can be determined using routine methods for any particular reagent.

The drying step (iii) above may be carried out using conventional methods, for example by freeze drying, spray drying, flash crystallisation, air stream drying (for example on a fluidised bed), vacuum drying, oven drying or any other method known in the art. Although the mechanical properties of the products of these two processes may be different, with the product of a spray drying process being a discrete and frequently flowable powder, and freeze drying producing a solid cake, the properties of the liposomes on rehydration in terms of their stability and entrapment is broadly similar.

For many applications, including the production of pharmaceutical compositions, spray drying may be preferable as a result of the suitability of the mechanical properties of the product for further processing.

The product of freeze-drying comprises a block of porous cake which has relatively poor mechanical properties. The use of jet milling of the cake to achieve better properties can be effected, but damage can occur in this additional step.

Spray drying can achieve a dry product with good mechanical properties that can be delivered by inhalation, or reconstituted in water and administered by the parenteral route.

The subsequent rehydration step may be carried out during the manufacture process or alternatively, the composition may be supplied in the dry state and rehydrated at the site of intended use, for example in the hospital or pharmacy where an encapsulated pharmaceutical is to be administered to patients.

The liposomes obtained have a good stability resulting in a long shelf life of the product. This is important for example for cosmetics, toiletries and pharmaceuticals.

As discussed above, the method is particularly suitable in the preparation of relatively small liposomes with a high loading of reagent. This is particularly desirable for pharmaceutical applications such as the delivery of materials such as polymeric or protein drugs, DNA vaccines, gene therapy vectors or chemicals. Suitable chemicals include antibiotics such as oxytetraclines, β-lactam antibiotics such as penicillins such as penicillin G, ampicillin or amoxycillin, or cephalosporins, anticancer drugs, hormones, immunotherapy agents, antiviral agents, anti-inflammatory compounds etc.

Liposome products obtained using the above described method may be formulated as pharmaceutical compositions, for example by combining them with pharmaceutically acceptable carriers or excipients. The formulations may be suitable for oral, parenteral in particular intravenous, or topical application, for example to the skin or to mucosal surfaces. A particular useful composition of the invention is a composition which is suitable for application by aerosol or inhaler. For this purpose, it has been found that high phase transition neutral lipid-based liposomes such as those formed from mixtures of DSPC and cholesterol are suitable. When produced in accordance with the invention, extrusion prior to drying may not be necessary.

BRIEF DESCRIPTION OF THE DRAWINGS

The invention will now be particularly described by way of example with reference to the accompanying diagrammatic drawings in which:

FIG. 5 is a graph showing the size distribution of extruded and freeze-dried liposomes obtained by the method of the invention encapsulating carboxyfluorescein (CF); and FIG. 6 is a graph showing the size distribution of various liposome compositions of the invention.

Figure 1:
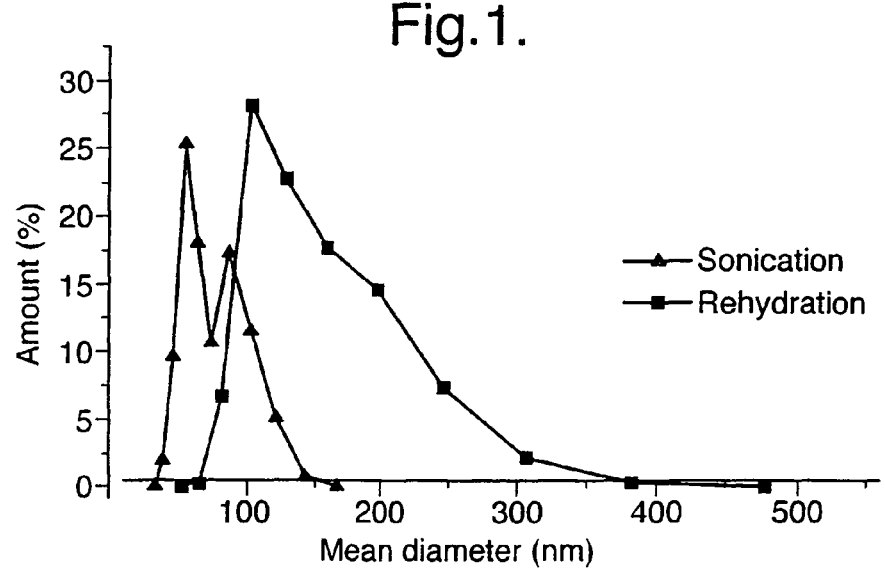
FIG. 1 is a graph showing the size evolution of dipalmitoyl phosphatidylcholine (DPPC) and cholesterol (CHOL) liposomes from sonication to freeze drying in the presence of 0.0357M sucrose, and rehydration.

In the following examples, egg phosphatidylcholine (PC), dipalmitoyl phosphatidylcholine (DPPC) and distearoyl phosphatidincholine (DSPC) were purchased from Lipoid GmbH, Ludwigshafen, Germany, cholesterol, carboxyfluorescein (CF), fluorescein isothiocyanate labelled albumin (FITC-albumin), riboflavin, daunorubicin, doxorubicin, Triton X-100, sucrose, glucose and sodium dodecylsulfate (SDS) from Sigma London. Epidermal growth factor (EGF) was a gift from the Centre of Biological Sciences Havana, Cuba. $Na^{125}I$, $C^{14}$-labelled hydroxypropyl-β-cyclodextrin, $^{14}C$-labelled penicillin were purchased from Amersham International (Amersham, UK). Labelling EGF with $^{125}I$ was done according to the chloramine T method. All other reagents were of analytical grade.

EXAMPLE 1

Freeze Drying Method

Solute-containing DRV liposomes were prepared as follows: Various lipid mixtures, in particular mixtures of PC:CHOL and DPPC:CHOL in a molar ratio of 1:1 were dissolved in chloroform. Following evaporation of the solvent in a rotary evaporator at 37° C., a film was formed on the wall of a round-bottomed spherical flask. Multilamellar vesicles (MLV) were generated by dispersing the lipid film at temperatures in excess of the lipid transition temperature (>Tc) (which was in some cases room temperature) with double distilled water. The suspension was adequately sonicated to produce small unilamellar vesicles (SUV) which were centrifuged to remove the metallic particles.

The SUV suspension was then transferred in a vial in which the desired amount of a selected drug (either FITC-Albumin (1 mg), CF (1 mg), hydroxypropyl-β-cyclodextrin (2 mg) or EGF (150 μg)) in solution was added as well as 0.0357M sucrose, and water added so as to attain the desired molarity of sucrose.

The preparation was then frozen and then freeze-dried over a sufficient time (according to the final volume). The dry cake was then subjected to controlled re-hydration at a temperature>Tc (e.g. 60° C.) for 15 mins. by adding 100 μl of distilled water. The preparation was diluted in PBS to have a specific gravity allowing the separation of the free drug from liposomes by ultracentrifugation.

Liposome size after rehydration was determined by photon correlation spectroscopy using an Autosizer 2C-Malvern (Malvern Instruments UK), equipped with a 25 mw helium/neon laser. Mean diameter and size distribution were obtained.

Z average mean diameters, polydispersity index cumulative and differential distribution were recorded as function of the sucrose molarity or where the DRVs were extruded, according to their size. For the preparations exhibiting large size (up to 6 microns), a Mastersizer (Malvern) was used.

Entrapment values for the drugs were determined after ultracentrifugation of liposomes at 40,000×g. The amount of encapsulated material was calculated as percent of total CF, FITC-albumin, EGF or hydroxypropyl-β-cyclodextrin used.

Total and encapsulated amount of carboxyfluorescein and FITC-albumin were measured by fluorescence photometry at λ emission=486 nm and λ excitation=514 nm for CF and λ emission=495 nm and λ excitation=520 nm for FITC-albumin from the pellet dissolved with Triton or SDS (5% final concentration). The carbon 14 emission from labelled hydroxypropyl-β-cyclodextrin was measured by assay of radioactivity in a β scintillation counter.

The results are shown in Table 1:

TABLE 1

| Entrapped material | Sucrose Molarity | Size after rehydration ± (SD) nm | % entrapment ± (SD) |
|---|---|---|---|
| FITC-Albumin* | 40 mM | 286.9 (29.2) | 87.5 (0.5) |
| | 65 mM | 265.4 (6) | 70.2 (8.5) |
| | 135 mM | 254.8 (6.5) | 52.7 (2.3) |
| | without sucrose | 5250 (25) | 84.2 (2.7) |
| Carboxy-fluorescein# | 35.7 mM | 163.8 (25) | 31.5 (0.1) |
| | 71.4 mM | 124.9 (2) | 30.75 (0.05) |
| | 135 mM | 129.35 (1) | 30.7 (0.05) |
| | without sucrose | 6200 (40) | 55.45 (0.05) |
| EGF# | 35.7 mM | 144.8 (32) | 33.5 (6.9) |
| EGF** | 64.6 mM | 167.4 (6.8) | 42 (1.5) |
| EGF# | 126 mM | 146.4 (1.3) | 29.6 (1) |
| EGF# | without sucrose | 1276.7 (100.7) | 22.3 (2.10) |
| EGF⊕ | 35.7 mM | 127.6 (2.8) | 25.5 (0.2) |
| EGF⊕ | without sucrose | 2495.7 (329) | 31.9 (0.85) |
| Hydroxypropyl-β-cyclodextrin# | 40 mm | 133 | 26 |
| | without sucrose | 10,000 | 24.4 | where * indicates a liposome formed from a mixture of 32:32 μmoles PC:CHOL;
= 16:16 μmoles PC:CHOL;
**+ 64:64 μmoles PC:CHOL; and
⊕= 16:16 μmoles DPPC:CHOL The results show that at a moderate degree of stabilization by sucrose, reconstitution allowing a certain extent of fusion (FIG. 1) can lead to a quite high percentage entrapment.

Although similar percentage encapsulation of FITC-Albumin was achieved in the presence or absence of 40 mM of sucrose, (87% and 84% respectively) the final size was much smaller for the preparation where sucrose was used.

Figure 2:
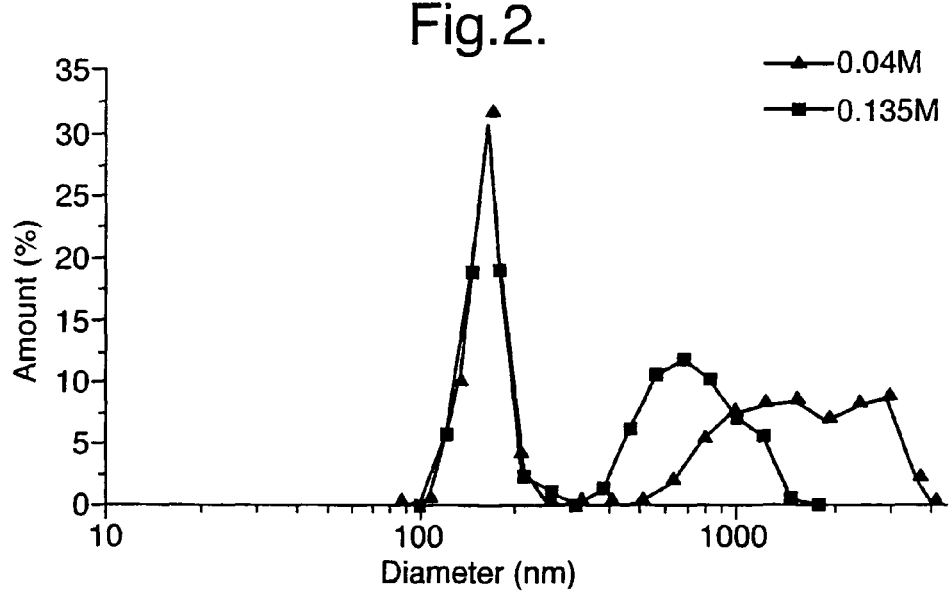
FIG. 2 is a graph illustrating the effect in the method of the invention of the molarity of sucrose on the PC:CHOL liposomes entrapping FITC-Albumin, on the size distribution (% distribution: intensity) obtained after freeze-drying and rehydration.

By varying the molarity of sucrose in different preparations of FITC-albumin containing-liposomes (Table 1), different size distributions of the liposomes could be obtained (FIG. 2) although entrapment values decreased with increasing molarity.

Encapsulation of EGF and CF was performed in the presence of sucrose at different molarities. The percentage entrapment values were equal to those obtained with other preparations using the same amount of lipids but performed in the absence of sucrose. (c.f. Table 1) In this case, the molarity of sucrose did not affect the percentage entrapment values but did impact on the sizes and size distribution (FIG. 3).

The Z average diameters of DRV liposomes produced in the presence or absence of sucrose are presented in Table 1. Results show that smaller vesicle size is achieved when sucrose is used at high molarity corresponding to narrower size distribution and so to moderate percentage entrapment values. The values of percentage entrapment are proportional to the size and size distribution width.

Figure 3:
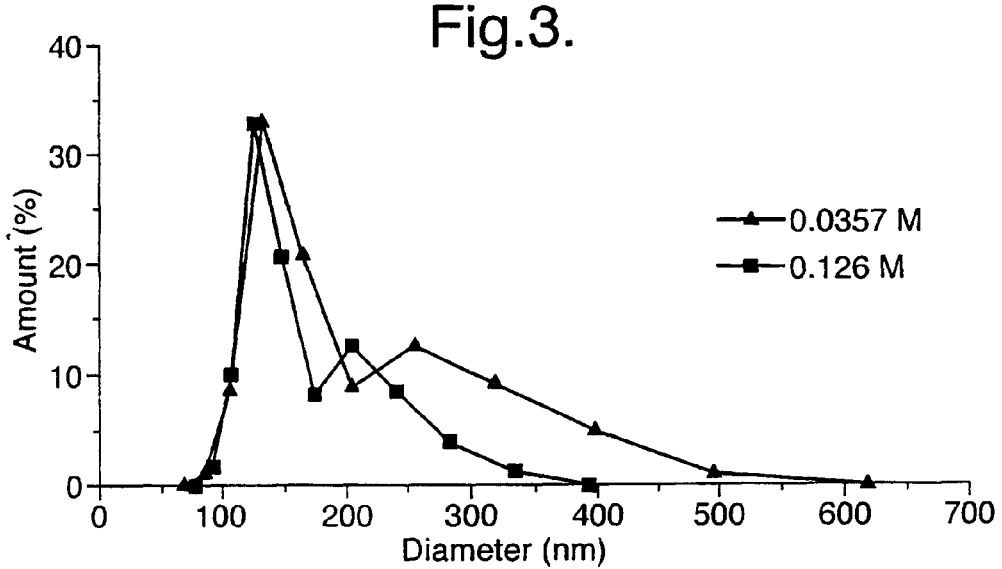
FIG. 3 is a graph showing the effect on the method of the invention of sucrose molarity on the size distribution after rehydration of PC:CHOL liposomes entrapping epidermal growth factor (EGF)

At two different molarities of sucrose we can measure almost the same two average diameters of two populations of vesicles which have got different widths (FIG. 3).

For liposomes entrapping EGF prepared at 35.70 mM and 126 mM of sucrose the two average diameters after rehydration were 144.8±32 nm and 146.4±1.3 nm respectively.

If we look at the size distribution we observe that it is narrower for the 126 mM sucrose preparation. Decreasing the size of liposomes and narrowing the size distribution by using high molarity of sucrose (over 36 mM) does not induce low entrapment values. Using two different concentrations of sucrose (35.7 mM and 135 mM), it was found that liposomes entrapping the same amount of CF (around 30%) with narrower size distribution (PDI=0.13) could be prepared than with liposomes prepared at 135 mM sucrose.

EXAMPLE 2

Comparison of Liposomes of the Invention with Extruded Liposomes

In order to compare the method of the invention with that of extrusion, which also leads to vesicle size reduction, we used an extruder to treat DRV liposomes prepared without using sucrose. Liposomes prepared as described in Example 1 was compared to those obtained by an extrusion process.

DRV liposomes, prepared without sucrose were subjected to extrusion using a high pressure filter holder. Liposomes before the elimination of non-entrapped solute, were passed through polycarbonate membranes whose pore size were 1.2 µm., 0.4 µm., 0.2 µm. and 0.1 µm. At each extrusion step, five passes through the same membranes were accomplished.

The free solute was then separated from the extruded vesicles by ultracentrifugation. The pellet was suspended in 1 ml of PBS (PH=7.4).

Figure 4:
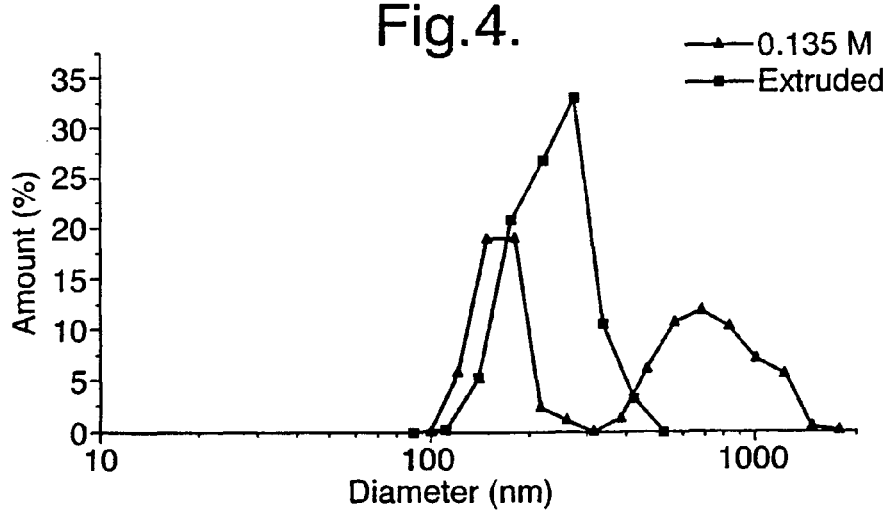
FIG. 4 is a graph showing a comparison of the size distribution of extruded and rehydrated PC:CHOL liposomes produced according to the invention, entrapping FITC-albumin.

The size of the liposomes were then measured as described in Example 1. The size distribution was compared with that of similar liposomes obtained as described in Example 1. The results are shown in FIGS. 4 and 5. It was found that the extruded liposomes demonstrated a narrower distribution of vesicle sizes.

The entrapment of material within the comparative liposomes was measured both before and after extrusion. The results are shown in Table 2.

TABLE 2

| Membrane pore size (nm) | reagent material | size before extrusion ± (SD) | size after extrusion ± (SD) | final % entrapment ± (SD) |
|---|---|---|---|---|
| 200 | FITC-albumin | 5250 (25) | 210.75 (4) | 29 (2) |
| 200 | CF | 6300 (150) | 213.9 (0.7) | 6.3 (1) |
| 100 | CF | 6220 (130) | 158.7 (0.3) | 6 (0.5) |
| 400 | EGF | 2495 (329) | 327.4 (12.68) | 9.15 (0.35) |
| 200 | EGF | 3128 (763) | 220.7 (4.12) | 6.35 (1.25) |

The average diameters and entrapment values are presented in Table 2. They show that low entrapment values and narrow size distribution (PDI≤0.1) are obtained for extruded liposomes. The low entrapment values combined with the requirement for an additional step (extrusion) for the preparation of small sized liposomes significant reduces the practical application of this method.

FIG. 5 shows an overlaid size distribution of extruded liposomes entrapping CF (6% entrapment) and of freeze-dried liposomes in presence of 135 mM sucrose with 30% of CF encapsulated.

The narrow distribution of vesicle size obtained with extrusion is not of prime importance since the corresponding percentage entrapment values are poor.

EXAMPLE 3

Size Distribution of Liposomes of the Invention

The use of phospholipids with a high phase transition temperature can allow the improvement of this technique concerning size distribution width. This was achieved when equimolar DPPC:CHOL liposomes entrapping EGF were formulated as described in Example 1 in the presence of 35.71 mM sucrose. EGF entrapment values were 25%. However, liposomes exhibited a narrower size distribution (Z average=128 nm) than the corresponding PC:CHOL preparation. The results are shown in FIG. 6. Thus it appears that, in this case, selection of lipids with high phase transition temperatures is preferred in order to achieve liposomes with a narrow size distribution.

EXAMPLE 4

High Yield Entrapment of Riboflavin into Small Liposomes

Equimolar phosphatidylcholine (390 µmoles) and cholesterol were used to prepare small unilamellar vesicles (SUV) by sonication. SUV were then mixed with riboflavin (12 mg) and increasing amounts of sucrose (0-5 mg per mg of total lipid). The mixtures were spray dried and then rehydrated. Drug entrapment was measured in the suspended pellets of the centrifuged preparations. The size of SUV in the final vesicle preparations was measured by photocorrelation spectroscopy or in a Mastersizer. Results are shown in Table 3.

TABLE 3

| SUV z average mean size (nm ± SD) | Amount of sucrose/amount of lipid | Entrapment (% of drug used) | Vesicle z average mean size (nm ± SD) |
|---|---|---|---|
| 78.1 ± 0.5 | 0 | 45.8% | 4690 |
| 77.0 ± 0.4 | 1 | 47.5% | 313.2 ± 1.5 |
| 67.0 ± 0.1 | 3 | 18.8% | 155.4 ± 1.5 |
| 80.5 ± 0.9 | 5 | 11.0% | 106.8 ± 1.5 |

It appears that spray-drying of small liposomes (SUV) in the presence of drug and sucrose (1 mg/1 mg lipid) leads to relatively small liposomes entrapping nearly half (47.5%) of the amount of drug used. By increasing the amount of sucrose present, vesicle size is reduced further with, however, a concomitant reduction of entrapment values.

EXAMPLE 5

Liposomes Containing Glucose

The procedure of Example 1 was repeated but using riboflavin as the active agent in an amount to give a concentration in the solution of 1 mg (total in 1 ml) and, in some instances, using glucose in place of sucrose. Liposome size on rehydration was measured as described in Example 1. The riboflavin encapsulation efficiency was calculated by measuring total and encapsulated riboflavin by fluorescence photometry at emission wavelength=480 nm and excitation wavelength=520 nm. The results are shown in Tables 4 and 5.

TABLE 4

| Sucrose/lipid Mass ratio | Size (nm) | Glucose/lipid Mass ratio | Size (nm) |
|---|---|---|---|
| 0/1 | 1243.4 | 0/1 | 5210 |
| 1/1 | 591.8 | 1/1 | 908 |
| 3/1 | 168.9 | 3/1 | 306.8 |
| 5/1 | 144.9 | 5/1 | 267 |

TABLE 5

| Sucrose/lipid Mass ratio | % entrapment | Glucose/lipid Mass ratio | % entrapment |
|---|---|---|---|
| 0/1 | 59.3 | 0 | 45.87 |
| 1/1 | 78.0 | 1 | 52.97 |
| 3/1 | 47.83 | 3 | 45.21 |
| 5/1 | 34.81 | 5 | 39.4 |

In terms of quality, adding glucose to the SUV liposomes instead of sucrose produced the same stabilisation effect. The entrapment values of riboflavin were of a similar order in both lipid to sugar ratios of 3 g/g and 5 g/g of glucose or sucrose. (Table 5).

Liposomes prepared by adding the equivalent amount of glucose exhibited larger vesicles size upon rehydration compared to the samples prepared in presence of sucrose (Table 4).

EXAMPLE 6

Effect of Rehydration Temperature on Liposome Formation

The method of Example 1 was repeated using equimolar PC:CHOL liposomes, a sucrose solution (68.7 mM) and 5 mg $^{14}C$ penicillin (Pen G) as the active agent. In this case however, the rehydration was carried out at various temperatures. Specifically, some preparations were rehydrated at room temperature while others were heated at 60° C. for 15 min.

Entrapment efficiency was determined after ultracentrifugation of the prepared liposomes at 40,000 g, and then the radioactivity of the $^{14}C$-penicillin was expressed as a percentage of the total amount in the supernatant and the pellet. The results are shown in Table 6.

TABLE 6

| EPC: CHOL Rehydration @ 25° C. | | | | EPC: CHOL Rehydration @ 60° C. | | | |
|---|---|---|---|---|---|---|---|
| Sucrose mol = 68.7 mM SUV size = 68 nm | | | | Sucrose mol = 68.7 mM SUV: size = 85.8 nm | | | |
| Pen G Suc/lip | 5 mg Size (nm) | % entr | PDI | Pen G Suc/lip | 5 mg Size (nm) | % entr | PDI |
| 0/1 | 5605 | 38.5 | | | | | |
|  | 4920 | 45.5 | — | | | | |
| AV | 5262 | 42 | — | | | | |
| SD | 342.5 | 3.5 | — | | | | |
| 1 g/g | 95.7 | | 0.38 | | | | |
|  | 69.7 | | 0.38 | 1 g/g | 973 | | 0.12 |
|  | 95.7 | | 0.38 | | 926.4 | | 1.0 |
| AV | 96 | 12.9 | 0.38 | AV | 949.7 | 34.4 | 0.56 |
| SD | 0.47 | | 00 | SD | 23.3 | | 0.44 |
| 1 g/g | 104 | | 0.33 | | | | |
|  | 102.9 | | 0.4 | 1 g/g | 1135 | | 0.33 |
|  | 101.5 | | 0.43 | | 1063.4 | | 0.40 |
| AV | 102.8 | 14.1 | 0.39 | AV | 1099 | 40 | 0.36 |
| SD | 1.02 | | 0.04 | SD | 35.8 | | 0.03 |
| 3 g/g | 89.5 | | 0.24 | | | | |
|  | 92.8 | | 0.22 | 3 g/g | 232 | | 0.31 |
|  | 90.4 | | 0.21 | | 229 | | 0.29 |
| AV | 90.9 | 6.2 | 0.22 | AV | 230.5 | 24.1 | 0.3 |
| SD | 1.39 | | 0.01 | SD | 1.45 | | 0.01 |
| 3 g/g | 93.7 | | 0.2 | | | | |
|  | 88.8 | | 0.43 | 3 g/g | 247.7 | | 0.29 |
|  | 84.5 | | 0.53 | | 244.6 | | 0.27 |

TABLE 6-continued

| EPC: CHOL Rehydration @ 25° C. | | | | EPC: CHOL Rehydration @ 60° C. | | | |
|---|---|---|---|---|---|---|---|
| Sucrose mol = 68.7 mM SUV size = 68 nm | | | | Sucrose mol = 68.7 mM SUV: size = 85.8 nm | | | |
| Pen G Suc/lip | 5 mg Size (nm) | % entr | PDI | Pen G Suc/lip | 5 mg Size (nm) | % entr | PDI |
| AV | 89 | 6.1 | 0.39 | AV | 246.15 | 23.6 | 0.28 |
| SD | 3.76 | | 0.14 | SD | 1.55 | | 0.01 |
| 5 g/g | 88.8 | | 0.19 | | | | |
| | 92.1 | | 0.14 | 5 g/g | 271.6 | | 0.30 |
| | 90.9 | | 0.16 | | 276.2 | | 0.21 |
| AV | 90.6 | 6.3 | 0.16 | AV | 273.9 | 17.2 | 0.25 |
| SD | 1.36 | | 0.02 | SD | 2.3 | | 0.04 |
| 5 g/g | 89 | | 0.16 | | | | |
| | 88.7 | | 0.12 | 5 g/g | 268.3 | | 0.37 |
| | 86.9 | | 0.15 | | 266.3 | | 0.27 |
| AV | 88.2 | 6.9 | 0.14 | AV | 267.3 | 17.9 | 0.32 |
| SD | 0.93 | | 0.02 | SD | 1 | | 0.05 |

In the above table, as well as the following tables, "AV" represents the average liposome size, "SD" is the standard deviation and "PDI" represents size distribution or polydispersity index.

Liposomes which were rehydrated at room temperature showed only a slight increase in size from 68 nm (sonicated SUV) to only an average of 90 nm but allowed an encapsulation of an average of 6.5% of the originally added penicillin. Even at high concentrations of sucrose, a degree of encapsulation could be achieved. The 100 nm vesicles exhibit a percentage encapsulation of 14%.

Heating similar preparations during the rehydration step led to larger vesicles. Liposomes of an average diameter of 230 nm could encapsulate 24% of the originally added $^{14}C$ penicillin (ratio of 3 g sucrose/g of lipid). Increasing the amount of sucrose by increasing the mass ratio of sugar/lipid from 3 to 5 led to slightly larger vesicles exhibiting a lower percentage encapsulation.

EXAMPLE 7

Encapsulation of $^{14}C$ Penicillin in Various Sucrose Concentrations

The method of Example 6 was repeated using equimolar PC:CHOL liposomes and $^{14}C$ penicillin (5 mg) as the active agent but with either a high molarity sucrose solution (68.78 mM) or a more dilute sucrose solution (35 mM).

The results are shown in Table 7, side by side with the 25° C. rehydration results previously shown in Table 6.

TABLE 7

| EPC: CHOL Rehydration @ 25° C. Sucrose mol = 68.7 mM, SUV size = 68 nm | | | | EPC: CHOL Rehydration @ 25° C. Sucrose mol = 35 mM, SUV size = 83.5 nm | | | |
|---|---|---|---|---|---|---|---|
| Pen G Suc/lip | 5 mg Size(nm) | % entr | PDI | Pen G Suc/lip | 5mg Size(nm) | % entr | PDI |
| 0/1 | 5605 | 38.5 | — | | | | |
| | 4920 | 45.5 | — | | | | |
| AV | 5262.5 | 42 | — | | | | |
| SD | 342.5 | 3.5 | — | | | | |
| 1 g/g | 95.7 | | 0.38 | | | | |
| | 69.7 | | 0.38 | 1 g/g | 211.6 | | 0.3 |
| | 95.7 | | 0.38 | | 213.5 | | 0.34 |
| AV | 96 | 12.9 | 0.38 | AV | 212.55 | 29.1 | 0.32 |
| SD | 0.47 | | 00 | SD | 0.95 | | 0.02 |
| 1 g/g | 104 | | 0.33 | | | | |
| | 102.9 | | 0.4 | 1 g/g | 212.2 | | 0.25 |
| | 101.5 | | 0.43 | | 215.3 | | 0.27 |
| AV | 102.8 | 14.1 | 0.39 | AV | 213.75 | 31.8 | 0.26 |
| SD | 1.02 | | 0.04 | SD | 1.55 | | 0.01 |
| 3 g/g | 89.5 | | 0.24 | | | | |
| | 92.8 | | 0.22 | 3 g/g | 200.8 | | 0.06 |
| | 90.4 | | 0.21 | | 198.8 | | 0.09 |
| AV | 90.9 | 6.2 | 0.22 | AV | 199.8 | 19.9 | 0.075 |
| SD | 1.39 | | 0.01 | SD | 1 | | 0.015 |
| 3 g/g | 93.7 | | 0.2 | | | | |
| | 88.8 | | 0.43 | 3 g/g | 190 | | 0.2 |
| | 84.5 | | 0.53 | | 192.3 | | 0.16 |
| AV | 89 | 6.1 | 0.39 | AV | 191.15 | 19.0 | 0.18 |
| SD | 3.76 | | 0.14 | SD | 1.15 | | 0.02 |
| 5 g/g | 88.8 | | 0.19 | | | | |
| | 92.1 | | 0.14 | 5 g/g | 198.7 | | 0.04 |
| | 90.9 | | 0.16 | | 200 | | 0.1 |

TABLE 7-continued

| EPC: CHOL Rehydration @ 25° C. Sucrose mol = 68.7 mM, SUV size = 68 nm | | | | EPC: CHOL Rehydration @ 25° C. Sucrose mol = 35 mM, SUV size = 83.5 nm | | | |
|---|---|---|---|---|---|---|---|
| Pen G Suc/lip | 5 mg Size(nm) | % entr | PDI | Pen G Suc/lip | 5mg Size(nm) | % entr | PDI |
| AV | 90.6 | 6.3 | 0.16 | AV | 199.35 | 16.2 | 0.07 |
| SD | 1.36 | | 0.02 | SD | 0.65 | | 0.03 |
| 5 g/g | 89 | | 0.16 | | | | |
| | 88.7 | | 0.12 | 5 g/g | 195.2 | | 0.08 |
| | 86.9 | | 0.15 | | 196 | | 0.06 |
| AV | 88.2 | 6.9 | 0.14 | AV | 195.6 | 14.8 | 0.07 |
| SD | 0.93 | | 0.02 | SD | 0.4 | | 0.01 |

The liposomes produced using a low molarity sugar solution exhibited an average size around 200 nm, which was higher than those produced using high molarity sugar solution. However, the entrapment values were higher and polydispersity index lower.

It would appear therefore that decreasing the molarity of sucrose during liposome preparation is a better alternative to the use of high temperatures (c.f. Example 6) during the rehydration step in order to enhance entrapment. Although similar percentage encapsulation is achieved, the liposomes maintain smaller sizes when low molarity sucrose is used.

EXAMPLE 8

DSPC Liposome Preparation

The method of Example 6 was repeated using DSPC and equimolar cholesterol to prepare liposomes. In this experiment, a high sucrose molarity (71 mM) and penicillin (5 mg) was used.

The results are shown in Table 8.

TABLE 8

| DSPC:CHOL Heated at 60° C. for 15 min Sucrose molarity 71.16 mM SUV size (nm) 77.2 PDI = 0.27 | | | |
|---|---|---|---|
| Mass sugar/lipid | Size (nm) | % Encapsulation | PDI |
| 0/1 | 4645 | 50.35 | — |
| | 5005 | 51.43 | — |
| AV | 4825.0 | 50.9 | — |
| SD | 180.00 | 0.54 | — |
| 1 | 302 | | 0.17 |
| | 282 | | 0.34 |
| | 277.2 | | 0.3 |
| AV | 287.1 | 41.9 | 0.3 |
| SD | 10.74 | | 0.07 |
| 1 | 252.9 | | 0.28 |
| | 241.3 | | 0.25 |
| | 239.7 | | 0.27 |
| AV | 244.6 | 37.7 | 0.27 |
| SD | 5.88 | | 0.01 |
| 3 | 158 | | 0.08 |
| | 152.3 | | 0.18 |
| | 152.4 | | 0.15 |
| AV | 154.2 | 18.8 | 0.14 |
| SD | 2.66 | | 0.04 |
| 3 | 160.8 | | 0.18 |
| | 158.8 | | 0.14 |
| | 154.2 | | 0.17 |
| AV | 157.9 | 19.3 | 0.16 |
| SD | 2.78 | | 0.02 |
| 5 | 171.2 | | 0.1 |
| | 166.9 | | 0.14 |
| | 164.5 | | 0.12 |

TABLE 8-continued

| DSPC:CHOL Heated at 60° C. for 15 min Sucrose molarity 71.16 mM SUV size (nm) 77.2 PDI = 0.27 | | | |
|---|---|---|---|
| Mass sugar/lipid | Size (nm) | % Encapsulation | PDI |
| AV | 167.5 | 13.9 | 0.12 |
| SD | 2.77 | | 0.02 |
| 5 | 143.9 | | 0.13 |
| | 142.4 | | 0.11 |
| | 139.5 | | 0.14 |
| AV | 141.9 | 15.3 | 0.13 |
| SD | 1.83 | | 0.01 |

These results show that increasing the amount of sucrose resulted in decreased entrapment values of $^{14}C$ penicillin and decreasing average diameter. DSPC CHOL liposomes showed higher entrapment values and smaller sizes compared to PC:CHOL liposomes. This may be due to the high phase transition temperature (Tc) of DSPC allowing higher stability upon heating.

EXAMPLE 9

Doxorubicin Encapsulation

Doxorubicin containing liposomes were prepared using the experimental conditions set out in Table 9.

TABLE 9

| Experimental conditions | | | | |
|---|---|---|---|---|
| Doxorubicin (1.3 mg/ml) | | | | |
| Doxorubicin assay at excitation and emission wavelength of 480 nm and 560 nm respectively | | | | |
| Liposome Compositions | | | | |
| EPC:CHOL (38.2 mg total); vesicle size 68.2 nm Doxorubicin used 0.5 mg | | | | |
| Sucrose used (mg) | 0 | 38 | 114 | 190 |
| Volume before freeze drying (ml) | 1.51 | 1.51 | 4.5 | 7.5 |
| DSPC:CHOL (40 mg total); vesicle size 59.7 nm Doxorubicin used: 0.5 mg | | | | |
| Sucrose used (mg) | 0 | 40 | 120 | 200 |
| Volume before freeze drying (ml) | 1.58 | 1.58 | 4.73 | 7.9 |

The size of the rehydrated liposomes were determined as described in previous examples. Entrapment values for doxorubicin were determined after ultracentifugation as described above. Total and encapsulated doxorubicin were measured by fluorescence photometry at emission wavelength 490 nm and excitation wavelength 560 nm. The results are shown in Table 10.

TABLE 10

|  | Sucrose/lipid mass ratio | Entrapment | Size (nm) | PDI |
|---|---|---|---|---|
| EPC:CHOL | 0/1 | 53 | 2276 | 0.99 |
|  | 1/1 | 54.5 | 281.96 | 0.34 |
|  | 3/1 | 47.1 | 133.5 | 0.15 |
|  | 5/1 | 45.45 | 116.4 | 0.15 |
| DSPC:CHOL | 0/1 | 74 | 2373.8 | 1 |
|  | 1/1 | 71.6 | 686.9 | 0.51 |
|  | 3/1 | 67.95 | 179.53 | 0.28 |
|  | 5/1 | 66.4 | 131.23 | 0.11 |

Doxorubicin was successfully encapsulated in small-sized liposomes. Equimolar PC:CHOL liposomes prepared with 5 g sucrose to 1 g of lipid exhibited a size of 116 nm and an encapsulation efficiency of 45%. Increasing the sucrose to lipid ratio did not affect substantially the % encapsulation. Replacing PC with DSPC generated liposomes exhibiting higher percentage encapsulation.

EXAMPLE 10

Effects of Increasing Sucrose Concentration

The method of Example 4 was repeated using progressively higher concentrations of sucrose. The concentrations used together with the riboflavin entrapment figures and the liposome size results are shown in Table 11.

TABLE 11

The effect of sucrose concentration on the entrapment of riboflavin

| SUV | Size (nm) | Sucrose (mM) | Sucrose/lipid mass ratio (% w/v sugar) | Entrapment (% ± SD) | Size nm ± SD) | PDI ± SD |
|---|---|---|---|---|---|---|
| PC, CHOL | 57.0 | 0.0 | 0.0 | 43.7 | 5200 |  |
|  |  | 40.0 | 1.0 | 78.0 | 591.8 |  |
|  |  |  | 3.0 | 47.8 | 168.9 |  |
|  | 292.1 | 10.0 (10.0%) | | 6.1 ± 0.8 | 113.4 ± 3.4 | 0.12 ± 0.0 |
|  |  | 15.0 (10.0%) | | 4.1 ± 0.3 | 116.3 ± 0.4 | 0.14 ± 0.0 |

These results show that at high sucrose/lipid mass ratios, in particular in excess of 10% w/v sucrose, the entrapment figures are low, although the stabilisation effects on the size of the liposomes is good.

EXAMPLE 11

Desoxyfructo-Serotonin (DFS) Encapsulation

Liposomes containing DFS were prepared using the conditions summarised in Table 12 below. The results including the entrapment figures and the size after rehydration is also shown in this table.

TABLE 12

Desoxyfruco-serotonin (DFS) (input 2 mg)
Rehydrated at room temperature
Sucrose molarity = 52 mM

| Lipid composition | Sucrose/lipid mass ratio | % Entrapment (±SD) | Size (nm) (±SD) | PDI (±SD) |
|---|---|---|---|---|
| EPC:CHOL | none | 92.73 (0.23) | 1152.9 (60.6) | 1 (0) |
|  | 1 | 36.9 (0.42) | 121.1 (7) | 0.29 (0.01) |
|  | 5 | 12 (2.7) | 134.5 (24) | 0.15 (0.07) |

In this example, good levels of entrapment were achieved as well as acceptable size stabilisation.

The invention claimed is:

1. A method of entrapping a water-soluble drug into preformed liposomes, which method consists essentially of the steps of:
   (i) providing an aqueous suspension of empty liposomes, said liposomes consisting of phosphatidylcholines optionally in combination with phosphatidic acid or stearylamine and optionally in combination with cholesterol, said liposomes having an average diameter in the range 25 to 100 nm;
   (ii) mixing the empty liposomes from step (i) with a monosaccharide or disaccharide solution, having a concentration in the range 20-200 mM in an amount such that the mass ratio of monosaccharide or disaccharide to lipid is in the range 1:1 to 5:1, and an aqueous solution of said water-soluble drug to form a mixture;
   (iii) drying the mixture from step (ii) by spray drying, flash crystallizing, air-stream drying, vacuum drying, freeze-drying or oven drying; and
   (iv) rehydrating the dried product of step (iii) to form liposomes in which the drug is entrapped, whereby the liposomes formed in step (iv) have an average diameter which is higher than the average diameter of empty liposomes provided in step (i) and is in the range 100 to 200 nm,
   wherein at least 12% of the drug used in step (ii) is entrapped in step (iv).

2. A method according to claim 1 wherein the percentage of drug used in step (ii) which is entrapped during step (iv) is at least 30%.

3. A method according to claim 1 wherein the monosaccharide or disaccharide concentration is in the range 30 to 150 mM.

4. A method according to claim 1 wherein the monosaccharide or disaccharide is sucrose.

5. A method according to claim 1 wherein the monosaccharide or disaccharide is a monosaccharide which is glucose.

6. A method according to claim 1 wherein step (iii) is conducted by spray drying.

7. A method according to claim 1 wherein the said empty liposomes have an average diameter in the range 70 to 90 nm.

* * * * *